United States Patent [19]

Hockaday

[11] Patent Number: 5,012,540
[45] Date of Patent: May 7, 1991

[54] DISPOSABLE SHEET PROTECTIVE DEVICE

[76] Inventor: Susan D. Hockaday, 13038 Berlin St., Poway, Calif. 92064

[21] Appl. No.: 451,631

[22] Filed: Dec. 18, 1989

[51] Int. Cl.$^5$ .................. A47G 9/00; A61F 13/15
[52] U.S. Cl. ............................. 5/487; 5/484; 604/385.1; 604/389; 604/369
[58] Field of Search .............. 5/484, 487, 497, 502; 604/359, 369, 380, 385.1, 386, 389

[56] References Cited

U.S. PATENT DOCUMENTS

| | | | |
|---|---|---|---|
| 3,691,271 | 9/1972 | Charle et al. | 604/380 X |
| 4,216,774 | 8/1980 | Graber | 5/484 X |
| 4,286,002 | 8/1981 | Strong | 5/484 X |
| 4,381,782 | 5/1983 | Mazurak et al. | 604/369 X |
| 4,433,972 | 2/1984 | Malfitano | 604/385.1 |
| 4,759,754 | 7/1988 | Korpman | 604/389 X |
| 4,844,965 | 7/1989 | Foxman | 5/489 X |

*Primary Examiner*—Michael F. Trettel
*Attorney, Agent, or Firm*—Leon Gilden

[57] ABSTRACT

A disposable protective device is securable about individuals incontinent due to ill health, mental condition, or age. The device includes an impermeable sheet underlying a cushioned liquid absorbent layer coextensive with the sheet, wherein the laminated body includes a central body portion and longitudinally aligned first and second legs, wherein the first leg includes a plurality of adhesive members to secure the first and second legs about a body portion of an individual in a surrounding manner. The laminated body may include liquid soluble deodorant tablets as an embodiment of the invention, and may further include a cushioned buttocks pad formed with an undulating upper surface for accommodating a buttocks of an individual to enhance comfort of the device. A further embodiment may include a sloping ridged layer aligned orthogonally relative to a longitudinal axis of the device, wherein the ridge may include a cushioned liquid absorbent upper layer overlying a peaked cushion core for positioning between legs of an individual to enhance comfort in use of the device.

2 Claims, 4 Drawing Sheets

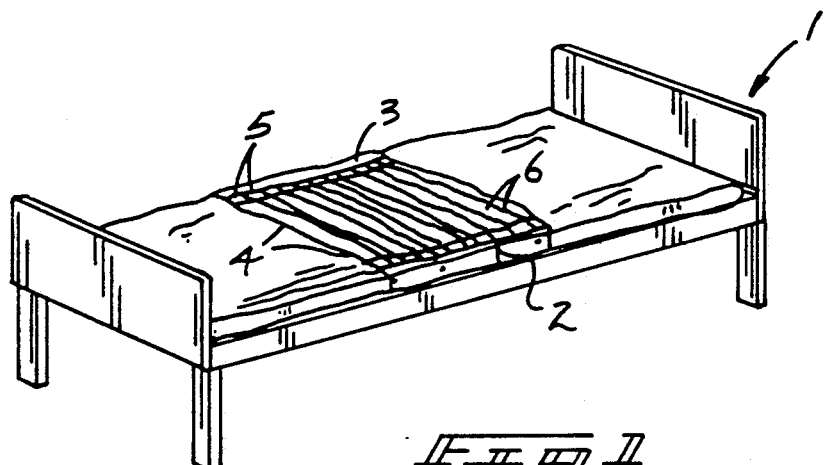
FIG 1
PRIOR ART
FIG 2
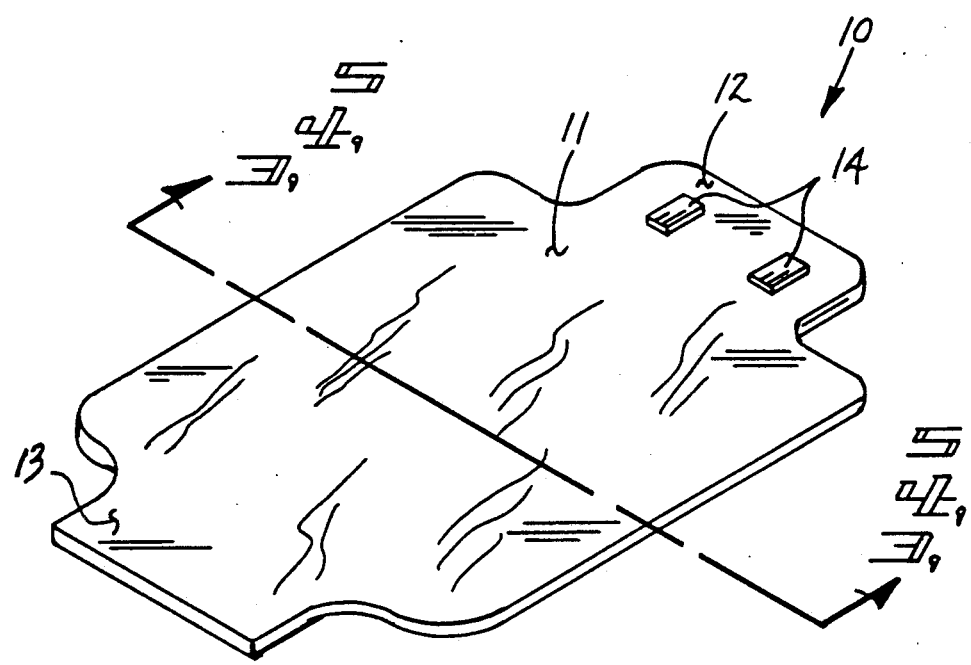

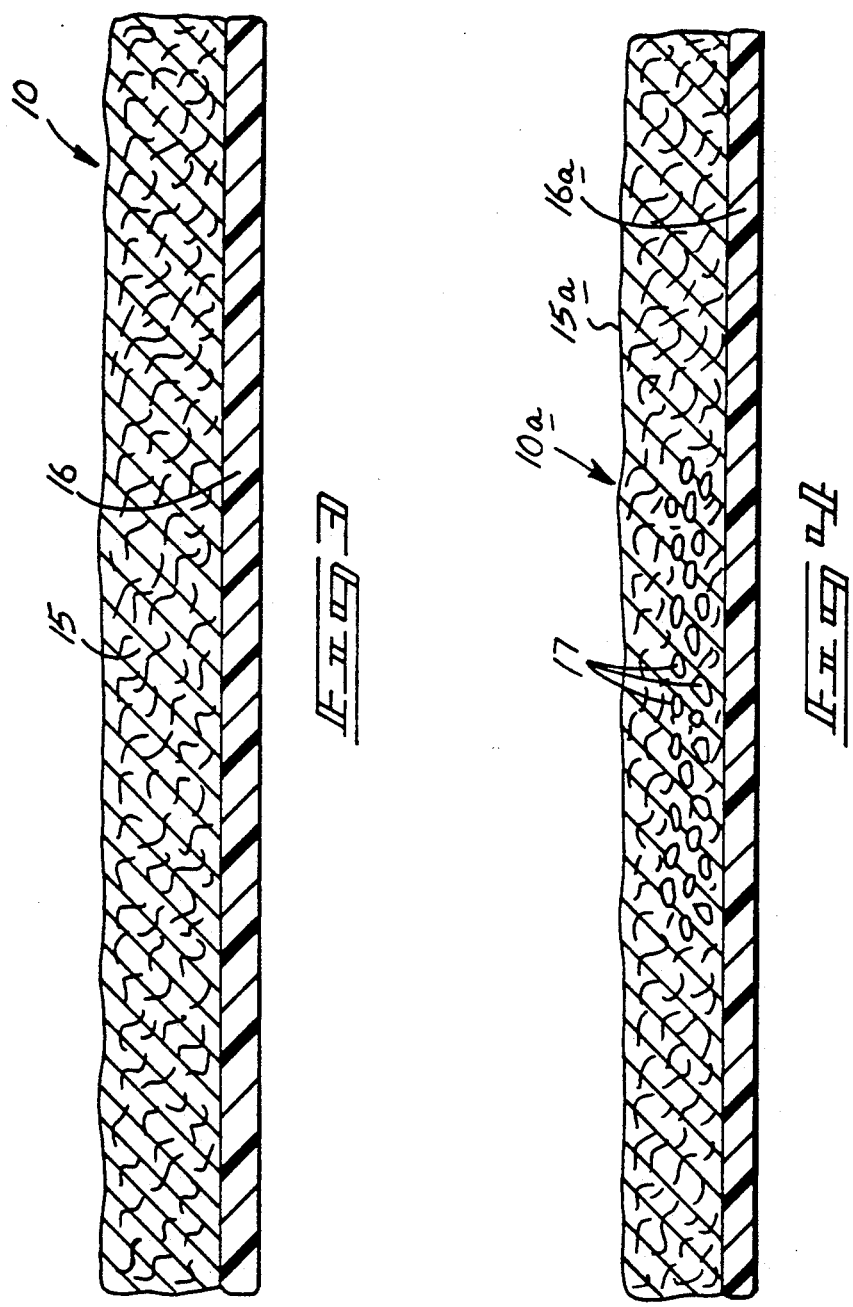

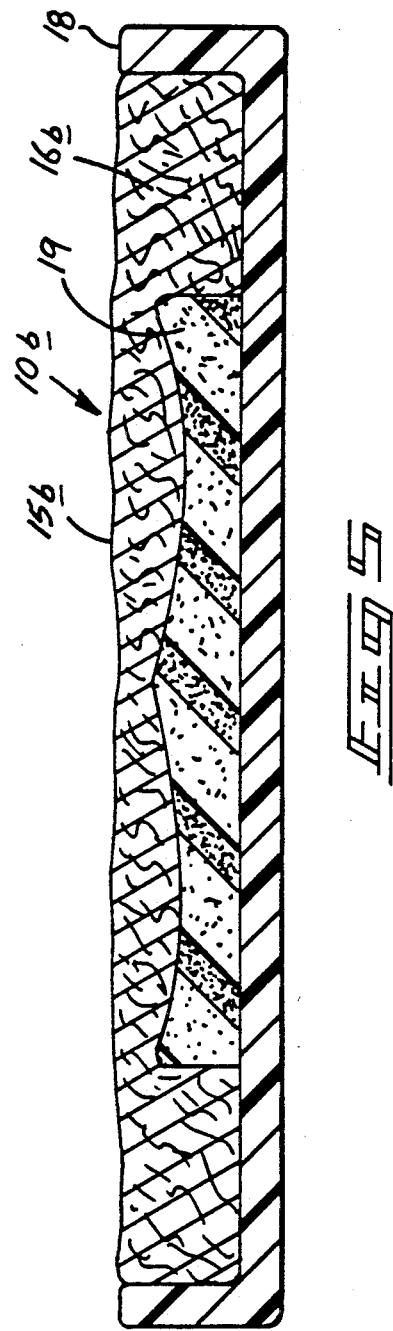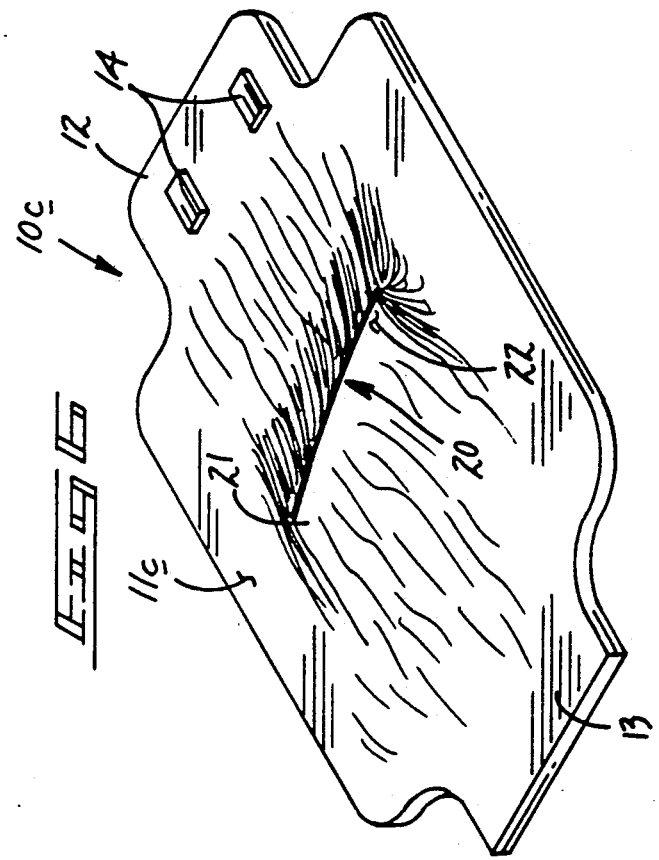

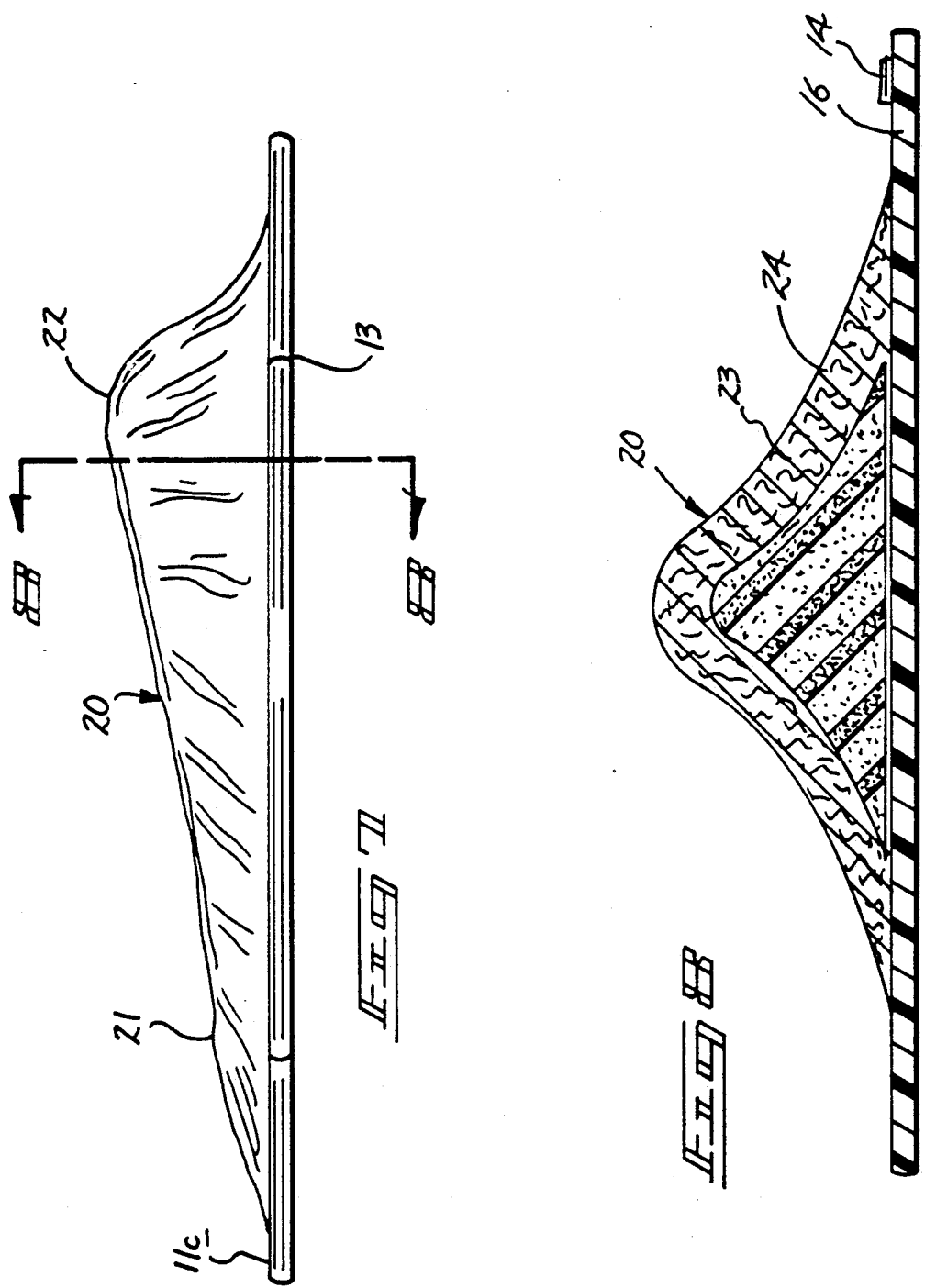

DISPOSABLE SHEET PROTECTIVE DEVICE

BACKGROUND OF THE INVENTION

1. Field of the Invention

The field of invention relates to protective devices for use in bedding, and more particularly pertains to a new and improved disposable sheet protective device wherein the same is securable in a surrounding manner about an individual for protection of bedding underneath the individual in use.

2. Description of the Prior Art

The use of various devices to protect bedding due to incontinence of individuals is known in the prior art. The prior art has employed a myriad of various devices to accomodate the physiology and geometric peculiarities of various individuals for protection of bedding. The devices have been of a type to overlie the bedding of a bed apparatus, or have been provided for securement to an individual for protection of the bedding. Examples of the prior art include U.S. Pat. No. 4,524,474 to Svensson setting forth the use of a pad provided with a lower liquid impermeable layer and an upper absorbent pad, wherein the pad is impregnated with filament members defining compartments for eliminating the spread of liquid throughout the device.

U.S. Pat. No. 4,286,002 to Strong sets forth a bodily fluid collection pad positionable between an individual and a mattress of an associated bed formed of an upper pad absorbing portion overlying a liquid impermeable layer.

U.S. Pat. No. 3,871,037 to Willington sets forth an incontinent pad arrangement wherein a relatively thin absorbing layer overlies an impervious layer with a thick absorbent layer and an impervious base layer, wherein the central impervious layer includes a window to permit fluid to pass therethrough to the relatively thick layer.

U.S. Pat. No. 3,965,503 to Gridel sets forth a protective mattress sheet wherein the waterproof fibers contain liquids by capillary action between a plurality of the layers including an upper wide meshed fabric layer and an underlying waterproof layer defining the pad arrangement.

U.S. Pat. No. 4,405,833 to Mesek sets forth an absorbent pad overlying a liquid impermeable pad wherein the relatively thick absorbing pad may be adhesively bonded to the impermeable pad, wherein a mixture of various fibers provides a unitary and stable configuration.

As such, it may be appreciated that there is a continuing need for a new and improved disposable sheet protective device as set forth by the instant invention which addresses both the problems of effectiveness in construction, as well as ease of use, and employment of the device about individuals requiring protection of underlying bedding, and in this respect, the present invention substantially fulfills this need.

SUMMARY OF THE INVENTION

In view of the foregoing disadvantages inherent in the known types of bedding protective devices now present in the prior art, the present invention provides a disposable sheet protective device securable about the torso and upper portion of an individual's legs to encompass the groin and buttocks region for protection of underlying bedding. As such, the general purpose of the present invention, which will be described subsequently in greater detail, is to provide a new and improved disposable sheet protective device which has all the advantages of the prior art protective bedding devices and none of the disadvantages.

To attain this, the present invention includes a disposable protective device securable about individuals incontinent due to ill health, mental condition, or age. The device includes an impermeable sheet underlying a cushioned liquid absorbent layer coextensive with the sheet, wherein the laminated body includes a central body portion and longitudinally aligned first and second legs, wherein the first leg includes a plurality of adhesive members to secure the first and second legs about a body portion of an individual in a surrounding manner. The laminated body may include liquid soluble deodorant tablets as an embodiment of the invention, and may further include a cushioned buttocks pad formed with undulating upper surface for accommodating a buttocks of an individual to enhance comfort of the device. A further embodiment may include a sloping ridged layer aligned orthogonally relative to a longitudinal axis of the device, wherein the ridge may include a cushioned liquid absorbent upper layer overlying a peaked cushion core for positioning between legs of an individual to enhance comfort in use of the device.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved disposable sheet protective device which has all the advantages of the prior art bedding protective devices and none of the disadvantages.

It is another object of the present invention to provide a new and improved disposable sheet protective device which may be easily and efficiently manufactured and marketed.

It is a further object of the present invention to provide a new and improved disposable sheet protective device which is of a durable and reliable construction.

An even further object of the present invention is to provide a new and improved disposable sheet protective device which is susceptible of a low cost of manufacture with regard to both materials and labor, and which accordingly is then susceptible of low prices of sale to the consuming public, thereby making such disposable sheet protective devices economically available to the buying public.

Still yet another object of the present invention is to provide a new and improved disposable sheet protective device which provides in the apparatuses and methods of the prior art some of the advantages thereof, while simultaneously overcoming some of the disadvantages normally associated therewith.

Still another object of the present invention is to provide a new and improved disposable sheet protective device wherein the same is securable about an individual during periods of need and subsequently disposable subsequent to its use.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an isometric illustration of a prior art device.

FIG. 2 is an isometric illustration of the instant invention.

FIG. 3 is a cross-sectional view taken along the lines 3—3 of FIG. 2 in the direction indicated by the arrows.

FIG. 4 is an orthographic cross-sectional view taken along the lines 4—4 of FIG. 2 in the direction indicated by the arrows.

FIG. 5 is an orthographic view taken along the lines 5—5 of FIG. 2 in the direction indicated by the arrows.

FIG. 6 is an isometric illustration of a further embodiment of the instant invention.

FIG. 7 is a side orthographic view taken in elevation of the embodiment as illustrated in FIG. 6.

FIG. 8 is an orthographic view taken along the lines 8—8 of FIG. 7 in the direction indicated by the arrows.

DESCRIPTION OF THE PREFERRED EMBODIMENT

With reference now to the drawings, and in particular to FIGS. 1 to 8 thereof, a new and improved disposable sheet protective device embodying the principles and concepts of the present invention and generally designated by the reference numerals 10, 10a, 10b, and 10c will be described.

FIG. 1 is illustrative of a prior art protective bag device 1 employing a liquid shielding layer 2 with an overlying absorbent layer 3, wherein the particular device as illustrated in FIG. 1 includes a series of flexible filaments 4 to define elongate compartments comprising first longitudinal compartments 5 and second lateral compartments 6 to define compartments for restricting flow of fluid directed into the absorbent layer 3.

The disposable sheet protective device 10 of the instant invention essentially comprises a central body 11 including a first longitudinally aligned leg portion 12 at one end of the central body and a second leg portion 13 longitudinally aligned with the central body 11 positioned at the opposed end of the central body 11, and wherein the first leg portion 12 includes a plurality of adhesive pads 14 for securing the first and central leg portions together for containment of an individual therewithin. It should be noted that the first and second leg portions are of a reduced width to that defined by the central body portion 11 to effectively define tabs for ease of securement of the leg portions together in an enveloping condition about an individual. The device accordingly is securable about the torso and upper portion of an individual's legs to encompass the groin and buttocks region for protection of underlying bedding.

FIG. 3 is illustrative of the basic protective device 10 in a cross-section therethrough comprising a cushioned liquid absorbent layer 15 of a substantially uniform thickness laminated to an underlying liquid impermeable sheet 16 coextensive with the layer 15. FIG. 4 is illustrative of a modification 10a wherein the cushioned liquid layer 15a mounted to an impermeable layer 16a includes a matrix of liquid soluble deodorant tablets 17 dispersed throughout the absorbent layer 15a operative to dispel offensive odors emanating as a result of liquid discharge from an individual into the device 10a.

FIG. 5 is a cross-sectional view through a further modified disposable sheet protective device 10b wherein a liquid absorbent layer 15b is again laminated to an underlying sheet 16b, wherein the sheet 16b includes integral side perimeter walls 18 to further contain liquid discharge within the layer 15b and contain the discharge therewithin. The absorbent layer 15b includes a buttocks shaped foam-type polymeric pad 19 including an undulating upper surface to conform to a buttocks of a human anatomy to enhance comfort of the device 10b in use.

FIG. 6 illustrates a yet further modified disposable sheet protective device 10c including a central absorbent ridge 20 medially positioned of the central body 11c and orthogonally aligned relative to a longitudinal axis of the central body 11c and the associated first and second respective legs 12 and 13. The central ridge 20 includes a lower end 21 sloping upwardly to an upper end 22 to be positioned between legs of a user of the device, wherein the ridge 20 includes an upper liquid absorbent ridge layer 23 of a generally triangular configuration overlying a central triangular cross-sectional configuration foam polymeric core 24 to provide comfort and cushioning in use of the device in securement about an individual.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A disposable bedding protective device comprising a flexible body member including a central, elongate body defined by a predetermined width including a first leg member extending longitudinally from a first end of the body member, and a second leg member extending longitudinally from a second end of the body member, wherein the first and second leg members are longitudinally aligned with the body member, and securement means mounted on an upper surface of the first leg member for selective securement to the second leg member, and the body member further including a top relatively thick liquid absorbent layer, and a relatively thin liquid impermeable sheet mounted to and underlying the top layer, and wherein the top layer is coextensively laminated to the bottom layer, and wherein the top layer includes a foam polymeric pad mounted medially of the top layer, wherein the polymeric pad is defined by an undulating upper surface to accommodate a buttocks of an individual positioned thereon, and the sheet includes side perimeter walls extending upwardly about a perimeter defined by the top layer.

2. A disposable bedding protective device comprising a flexible body member including a central, elongate body defined by a predetermined width including a first leg member extending longitudinally from a first end of the body member, and a second leg member extending longitudinally from a second end of the body member, wherein the first and second leg members are longitudinally aligned with the body member, and securement means mounted to an upper surface of the first leg member for selective securement to the second leg member, and the body member further including a top relatively thick liquid absorbent layer, and a relatively thin liquid impermeable sheet mounted to and underlying the top layer, and wherein the top layer is coextensively laminated to the bottom layer, and including a central absorbent ridge mounted medially of the body member and orthogonally aligned relative to a longitudinal axis directed through the body member and the leg members, and the ridge including a lower end sloping upwardly to an upper end of the ridge, and the ridge further including a relatively rigid polymeric core of a triangular cross-sectional configuration underlying the top layer.

* * * * *